(12) United States Patent
Preussner

(10) Patent No.: US 6,645,245 B1
(45) Date of Patent: Nov. 11, 2003

(54) ACCOMMODATIVE INTRAOCULAR LENS SYSTEM

(76) Inventor: Paul Rolf Preussner, Am Linsenberg 18, D-55131 Mainz (DE)

(*) Notice: Subject to any disclaimer, the term of this patent is extended or adjusted under 35 U.S.C. 154(b) by 0 days.

(21) Appl. No.: 09/869,509

(22) PCT Filed: Dec. 28, 1999

(86) PCT No.: PCT/DE99/04123
§ 371 (c)(1),
(2), (4) Date: Jun. 29, 2001

(87) PCT Pub. No.: WO00/45745
PCT Pub. Date: Aug. 10, 2000

(30) Foreign Application Priority Data

Feb. 1, 1999 (DE) .......................... 199 04 441

(51) Int. Cl.[7] .................................................. A61F 2/16
(52) U.S. Cl. ..................................... 623/6.22; 623/6.37
(58) Field of Search ............................. 623/6.22, 6.37

(56) References Cited

U.S. PATENT DOCUMENTS

| | | | |
|---|---|---|---|
| 4,298,996 A | * 11/1981 | Barnet | 623/6.43 |
| 5,108,429 A | * 4/1992 | Wiley | 623/6.22 |
| 5,171,266 A | * 12/1992 | Wiley et al. | 623/6.22 |
| 5,203,788 A | * 4/1993 | Wiley | 623/6.22 |
| 5,326,347 A | * 7/1994 | Cumming | 623/6.38 |
| 5,562,731 A | * 10/1996 | Cumming | 606/107 |
| 5,593,437 A | * 1/1997 | Arita et al. | 623/6.22 |
| 5,800,533 A | * 9/1998 | Eggleston et al. | 623/6.39 |

FOREIGN PATENT DOCUMENTS

| | | | |
|---|---|---|---|
| EP | 0337390 | * | 4/1989 |
| EP | 0356050 | * | 8/1989 |
| EP | 0493090 | * | 12/1991 |
| WO | 9615734 | * | 11/1995 |

\* cited by examiner

*Primary Examiner*—Corrine McDermott
*Assistant Examiner*—Thomas Sweet

(57) ABSTRACT

Disclosed is an implant for implantation in the human eye, which enables natural adjustment of the eye to different distances (accommodation) after cataract surgery (lens opacity). Permanent magnets (inner magnets) rest on the periphery of the intraocular lens located inside the capsular sack. Two additional permanent magnets that are fixed to the sclera (outer magnets) are located opposite to said inner magnets and slightly staggered to the back. The inner and outer magnets are polarized and geometrically disposed in such a way that they repel one another. Said repulsion effects a forward movement of the capsular sack and the lens located therein when the ciliary muscle contracts. Before placing the outer magnets, a measurement can be conducted with the aid of electromagnets whose strength can be regulated, whereby accommodation is determined as a function of the strength of the outer magnets. On the basis of the data obtained during said measurement, the strength, number, geometry and position of the outer (permanent) magnets can be selected.

5 Claims, 1 Drawing Sheet a  b

ACCOMMODATIVE INTRAOCULAR LENS SYSTEM

TECHNICAL FIELD

The invention is an intraocular lens with accompanying auxiliary devices by means of which a patient once again gains the capability of optical near vision (accommodation) through and after an operation on the natural lens.

STATE OF TECHNOLOGY

Intraocular lenses which are in accordance with the state of technology normally only allow sharp vision at exactly one distance. In addition, for some years, intraocular lenses have been known which have two or more focal distances ("multifocal lenses") and thus allow sharp vision at several distances. As several images are hereby superimposed indistinctly, the contrast with these lenses is markedly worse than with a monofocal lens. Also, it is only possible to see sharply at certain distances, the intermediate area is markedly more indistinct. Vision, as in the case of natural accommodation, can thus not be attained with these lenses.

Systems in which the refractive power of the intraocular implant can be adjusted by external measures represent an intermediate notional step towards accommodation. The optical elements can here be shifted on the optical axis by changing the posture of the head, by means of gravity or by magnetic forces (US5326347A, US5593437A). In the latter case, a magnetic layer is applied to the intraocular lens and the lens is moved by an adjustable magnet which is positioned in front of the eye in a kind of spectacles. In US5800533A, the shift on the optical axis is induced by means of a screw thread, whereby the screwing process is carried out by means of magnetic tools from outside of the eye.

The adjustability described above is not sufficient to restore an accommodation capability that is felt by the patient as being "natural" after the removal of the interior of his own, opaque lens (cataract). Instead, the refractive power of the implanted artificial lens has to be changed, for example, by means of its form or by shifting it along the optical axis, or by shifting several optical elements towards one another when the ciliary muscle contracts. Here below, only this process is intended to be understood under "accommodation". Several approaches have become known for implementing it. A balloon, that can be filled with liquid, can be inserted into the capsular bag (EP0493090A1). Two optically effective components can be shifted towards one another by hydrostatic pressure (IEP0356050B1). Optical components are shifted by means of spring pressure (EP0337390A2). In addition, there are intraocular lenses commercially available, the outer part of which (haptics) is formed as a springy hinge so that a radial contraction is turned into an axial shift (WO9615734A2).

None of the said approaches has been able to gain practical importance up to now. The reason is in principle the same for all of them: After removal of the interior of the lens, a shrinkage and hardening of the capsular bag occurs which differs greatly individually. The capsular bag can thus not be used as an element of a movement process of whatever kind that can be calculated in its mechanical parameters. In addition, the resilience of the zonula fibres, by which the capsular bag is suspended elastically from the ciliary muscle, also shows considerable fluctuations among individuals. Finally, for a large part of the patients it is to be expected that an opacification of the posterior capsule of the lens will occur after a cataract operation (secondary cataract). This opaque part must then be removed, for example with a laser, which once again drastically changes the mechanical properties of the capsular bag.

The object of this present invention is to make an intraocular lens available which changes its position in an axial direction on contraction of the ciliary muscle. The postoperative shrinkage of the capsular bag, the variation in the resilience of the zonula fibres and a later removal of the posterior, central part of the capsule (capsulotomy) are intended not to influence the function of the accommodation process substantially.

BRIEF DESCRIPTION OF THE INVENTION

The object is solved by the invention in accordance with claim 1. The intraocular implant, to be inserted into the capsular bag in the generally known manner, contains an artificial lens in generally known technology at its center permanent magnets on its peripheral part which are arranged in a circle, with the optical axis of the eye as the normal of the circle (hereinafter called "the inner magnets"). Opposite these inner magnets, permanent magnets are also fastened to the sclera in a circle lying further back, outside, the normal of the circle of which is once again the optical axis of the eye (hereinafter called "the outer magnets"). The inner and outer magnets are polarised in such a manner that they repel one another reciprocally, and are aligned geometrically in such a manner that this repulsion exercises a force directed towards the front of the capsular bag, and thus towards the intraocular lens located therein.

Figure 1:
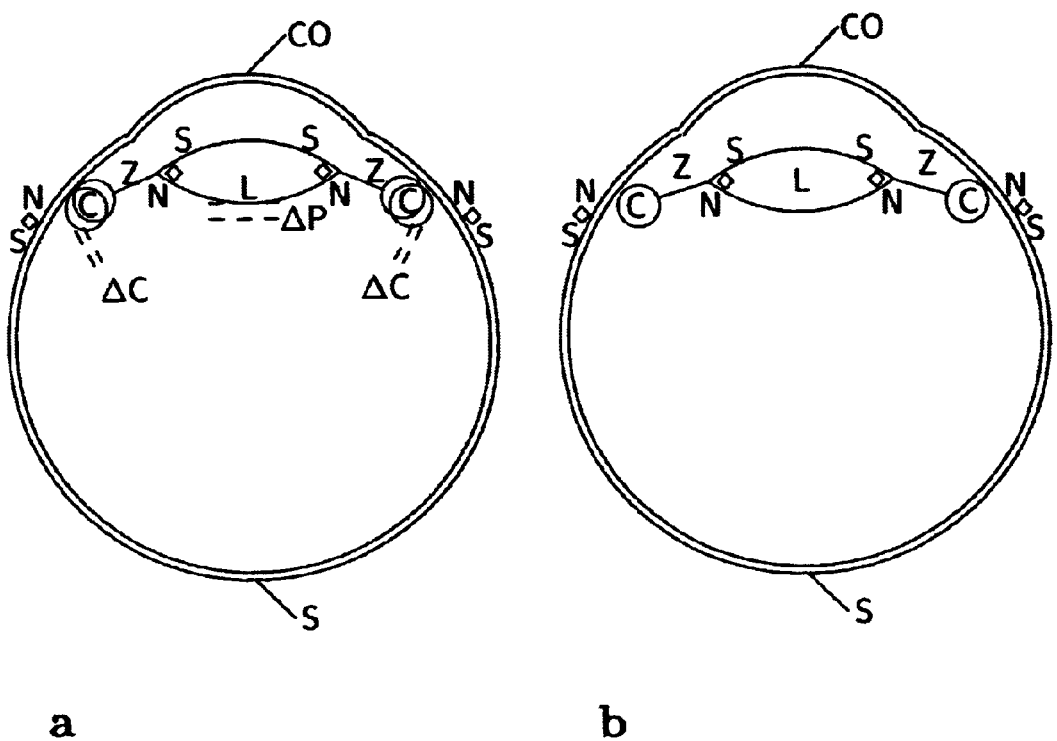
FIGS. 1a and 1b are cross sectional views of the intraocular lens of the current invention implanted into the human eye in both static and dynamic views, respectively.

In the specification, the following passage has been inserted immediately after the "Preferred execution and execution alternatives" (page 3).

Referring to FIGS. 1a and 1b, two schematic cross-sections of the human eye, each in a plane containing the optical axis, are shown with sclera S, cornea. Co, lens L, zonula Fibers Z and ciliary muscle C. Only the capsular bag of the lens is plotted. The nucleus and cortex of the lens are removed in a cataract operation. The artificial intraocular lens is not shown but assumed to be inside the capsular bag in a fixed position relative to it. Two little permanent magnets symbolized by $_N\Diamond^S$ and $^S\Diamond_N$ with N,S indicating the north and south pole of the magnetic polarization are fixed inside the capsular bag, in the following called "inner magnets". Two other permanent magnets symbolized by $_S\Diamond^N$ and $^N\Diamond_S$ with N,S indicating the north and south pole of the magnetic polarization are fixed at the sclera, in the following called "outer magnets". In the right subimage, the ciliary muscle is relaxed. In the left subimage, the ciliary muscle is contracted, indicated by the shift $\Delta C$. As inner and outer magnets polarized in such a way that they are repelling each other, the position the lens is shifted towards the cornea by $\Delta P$ due to the contraction of the ciliary muscle.

PREFERRED EXECUTION AND EXECUTION ALTERNATIVES

In its preferred execution, the implant to be inserted into the capsular bag is made up of any posterior chamber lens with central optics and preferably loop haptics in generally known and proven technology, as well as a capsule clamping ring, also in generally known and proven technology.

The inner magnets are cast in the capsule clamping ring. The magnets must be enclosed completely by biocompatible material. In order to reduce the density of the ring, the ring may contain hollow spaces between the inner magnets. The outer magnets may be executed as bar magnets, enclosed by biocompatible material, whereby ready-made eyelets, notches or threads, which have already been incorporated, facilitate the exact positioning and suturing. The outer magnets are preferably sutured from outside on the sclera under the conjunctiva. In principle, they can also be fastened inside the eye in the area of the pars plana. The latter is more favorable from the point of view of magnetic forces, but the operating risk is markedly higher.

In another version of the invention, the inner magnets are integrated into the haptics of the intraocular lens. In the case of loop haptics, for example, with C or J loops in generally known technology, the magnets can be inserted into the ends of the loops. The advantage of this version is the possibility of being able to execute these lenses as folded lenses in generally known technology. Admittedly, in this case only two inner magnets are possible, limiting the magnetic force. In the case of plate haptics, several magnets can be fitted in the outer area, but greater asymmetry in the shrinkage of the capsular bag is known to be a disadvantage here.

What is claimed is:

1. Accommodative intraocular lens system with
    an intraocular lens with an optical body and an optional haptics, insertable into the capsular bag,
    Permanent magnets which can be fitted inside the capsular bag at its periphery in a circle, the normal of which is the optical axis of the eye, hereinafter called inner magnets,
    Further magnets which can be fixed to the sclera outside or inside of the eye in a circle, the normal of which is the optical axis of the eye, hereinafter called outer magnets,
    A geometrical arrangement and a polarization of the magnets which is selectable in such a manner that the inner and outer magnets repel one another, and the force resulting from this is directed towards the cornea of the eye, pushing the capsular bag towards the cornea when the ciliary muscle contracts.

2. Accommodative intraocular lens system in accordance with claim 1, characterized by the fact that the inner magnets are integrated into a capsular tension ring.

3. Accommodative intraocular lens system in accordance with claim 1, characterized by the fact that hollow bodies are fixed to the inner magnets in order to reduce the density of the intraocular implant.

4. Accommodative intraocular lens system in accordance with claim 1, characterized by the fact that the inner magnets are integrated into the haptics of the intraocular lens.

5. Accommodative intraocular lens system in accordance with claim 1, characterized by the fact that eyelets, notches or suture material already fixed to the outer magnets are provided by the manufacturer in order to facilitate positioning and suturing during surgery.

* * * * *